United States Patent
Mcquillen et al.

(10) Patent No.: US 9,863,909 B2
(45) Date of Patent: Jan. 9, 2018

(54) OXYGEN SENSOR CONTROL BASED ON WATER CONTACT

(71) Applicant: Ford Global Technologies, LLC, Dearborn, MI (US)

(72) Inventors: Michael Mcquillen, Warren, MI (US); Gopichandra Surnilla, West Bloomfield, MI (US); Richard E. Soltis, Saline, MI (US); Daniel A. Makled, Dearborn, MI (US); Stephen B. Smith, Livonia, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 561 days.

(21) Appl. No.: 14/542,181

(22) Filed: Nov. 14, 2014

(65) Prior Publication Data

US 2016/0139073 A1    May 19, 2016

(51) Int. Cl.
  *G01N 27/409* (2006.01)
  *G01N 27/416* (2006.01)
  *G01N 27/406* (2006.01)

(52) U.S. Cl.
  CPC .................. *G01N 27/4067* (2013.01)

(58) Field of Classification Search
  CPC ............ G01N 27/4067; G01N 27/409; G01N 27/4163; G01N 27/41; G01K 17/00; F02D 2041/2058; F02D 41/1494; F02D 41/1454; F02D 41/1472; F02D 2400/14; F02D 41/1474
  See application file for complete search history.

(56) References Cited

U.S. PATENT DOCUMENTS

| 6,476,364 | B1 | 11/2002 | Shimamura et al. |
|---|---|---|---|
| 7,193,178 | B2 | 3/2007 | Sell et al. |
| 7,249,489 | B2 | 7/2007 | Allmendinger |
| 7,968,827 | B2 | 6/2011 | Adams et al. |
| 8,121,744 | B2 | 2/2012 | Sell et al. |
| 8,407,986 | B2 | 4/2013 | Hahn |
| 2002/0179443 | A1 | 12/2002 | Hada et al. |
| 2004/0173196 | A1 | 9/2004 | Hosoya et al. |
| 2007/0007134 | A1 | 1/2007 | Kawase et al. |
| 2007/0079597 | A1 | 4/2007 | Wang et al. |
| 2012/0273369 | A1* | 11/2012 | Kato ............... F02D 41/1454 205/775 |
| 2014/0076741 | A1 | 3/2014 | Adams |

FOREIGN PATENT DOCUMENTS

EP    2320219 A1    5/2011

OTHER PUBLICATIONS

Surnilla, Gopichandra et al., "Methods and Systems for Adjusting Heater Power of an Oxygen Sensor to Reduce Degradation from Water," U.S. Appl. No. 14/326,385, filed Jul. 8, 2014, 38 pages.
McQuillen, Michael et al., "Oxygen Sensor Control Responsive to Resistance and Impedance," U.S. Appl. No. 14/568,916, filed Dec. 12, 2014, 44 pages.

* cited by examiner

*Primary Examiner* — Gurpreet Kaur
(74) *Attorney, Agent, or Firm* — Julia Voutyras; McCoy Russell LLP

(57) ABSTRACT

Various methods for operating an oxygen sensor are provided. In one example, a method of operating an oxygen sensor comprises applying power to a heater of the oxygen sensor, and indicating whether water is in contact with the oxygen sensor based on a time rate of change of a temperature of the oxygen sensor.

19 Claims, 7 Drawing Sheets

OXYGEN SENSOR CONTROL BASED ON WATER CONTACT

FIELD

The field of the disclosure generally relates to oxygen sensor control.

BACKGROUND AND SUMMARY

Intake and/or exhaust gas sensors may be operated to provide indications of various gas constituents. Output from an oxygen sensor, for example, may be used to determine the air-fuel ratio (AFR) of exhaust gas. An oxygen sensor may be disposed in an engine intake passage to determine the concentration of exhaust gas recirculation (EGR) gasses in intake charge air. Indications of AFR may be used to adjust various engine operating parameters such as fueling and a target AFR, for example. In particular, exhaust gas AFR may be controlled to achieve the target AFR in order to maximize operating efficiency of an emission control device. For some oxygen sensors, their output may significantly vary as a function of their operating temperature. As such, these oxygen sensors may be heated by a heating element to achieve a desired operating temperature range such that desired oxygen sensing is provided.

In some approaches, the impedance of an oxygen sensor is used to control the temperature of the oxygen sensor. For example, closed loop control may be employed to control the oxygen sensor temperature, where the sensor temperature is determined based on the impedance of an oxygen sensing element (e.g., a concentration cell) in the oxygen sensor.

The inventors herein have recognized that the impedance of such an oxygen sensing element can rise exponentially as the temperature of the sensing element decreases. As such, the impedance may be prohibitively high for determining the oxygen sensor temperature in certain temperature ranges.

Other factors pose challenges to oxygen sensor control. Thermal shock and cracking, for example, can occur in an oxygen sensor when heated while water is in contact with the sensor. High rates of heating, rapid increases to high rates of heating, and sustained heating particularly increase the incidence of such issues, which can degrade oxygen sensing and thus engine operation. Accordingly, some approaches to oxygen sensor control wait to heat an oxygen sensor until exhaust gas reaches a dew point temperature at which it is assumed that water in the exhaust system evaporates. Once the dew point temperature has been reached, the oxygen sensor temperature may be controlled via closed loop control, for example.

The inventors herein have recognized several issues with such an approach. Specifically, unevaporated water may remain in contact with the oxygen sensor upon reaching, or in some cases exceeding, the dew point temperature. This water may be puddled water accumulated on the oxygen sensor, mixed with exhaust gas, and/or generally present in the exhaust system, for example. Moreover, even with water fully evaporated off the oxygen sensor, additional water may subsequently impinge upon the sensor, for example in the event of water splash. If at this point the oxygen sensor temperature is controlled via closed loop control, a water splash will reduce the sensor temperature, prompting a rapid increase to high levels of heating by closed loop control, which may lead to thermal shock and cracking in the sensor.

Other approaches to oxygen sensor control attempt to actively detect water impingement on an oxygen sensor based on pumping current. Pumping current is the electrical current that results from electrochemically pumping a substance (e.g., oxygen) out of or into a concentration cell by applying a pumping voltage across the concentration cell (e.g., across two electrodes of the cell), and may be proportional to the substance within the concentration cell, yielding an indication of the concentration of the substance.

The inventors herein have recognized an issue with such an approach. Pumping current may be insufficient to detect water impingement on an oxygen sensor placed in an exhaust system. Specifically, the pumping current of such an oxygen sensor may remain around zero, since the concentration of oxygen in exhaust gas remains near zero during normal operating conditions, which is insufficient for water impingement detection. While in some approaches the pumping voltage is varied, this voltage is typically varied only for small durations under specific conditions, both of which are unsuitable for detecting water impingement.

One approach that at least partially addresses the above issues includes a method of operating an oxygen sensor comprising applying power to a heater of the oxygen sensor, and indicating whether water is in contact with the oxygen sensor based on a time rate of change of a temperature of the oxygen sensor.

In a more specific example, indicating whether water is in contact with the oxygen sensor includes indicating that water is in contact with the oxygen sensor responsive to the time rate of change being less than a minimum expected time rate of change of the temperature of the oxygen sensor expected for the power applied to the heater.

In another example, the method further comprises, prior to indicating whether water is in contact with the oxygen sensor, determining the temperature of the oxygen sensor based on only a resistance of the heater if the resistance indicates a temperature below or equal to a threshold temperature, and both the resistance of the heater and an impedance of the oxygen sensor if the resistance indicates a temperature above the threshold temperature.

In yet another example, the power is a first power level, and the method further comprises, responsive to indicating that water is in contact with the oxygen sensor, applying a second power level greater than the first power level to the heater, and determining whether one of an expected temperature and a minimum expected time rate of change of the temperature of the oxygen sensor is reached by the oxygen sensor, the expected temperature and the minimum expected time rate of change both expected for the second power level.

In this way, both the temperature of, and water impingement on, an oxygen sensor may be determined throughout its operational range, enabling appropriate actions that maintain desired oxygen sensor operation to be taken whether water contact on the sensor is detected or not. Thus, the technical result is achieved by these actions.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
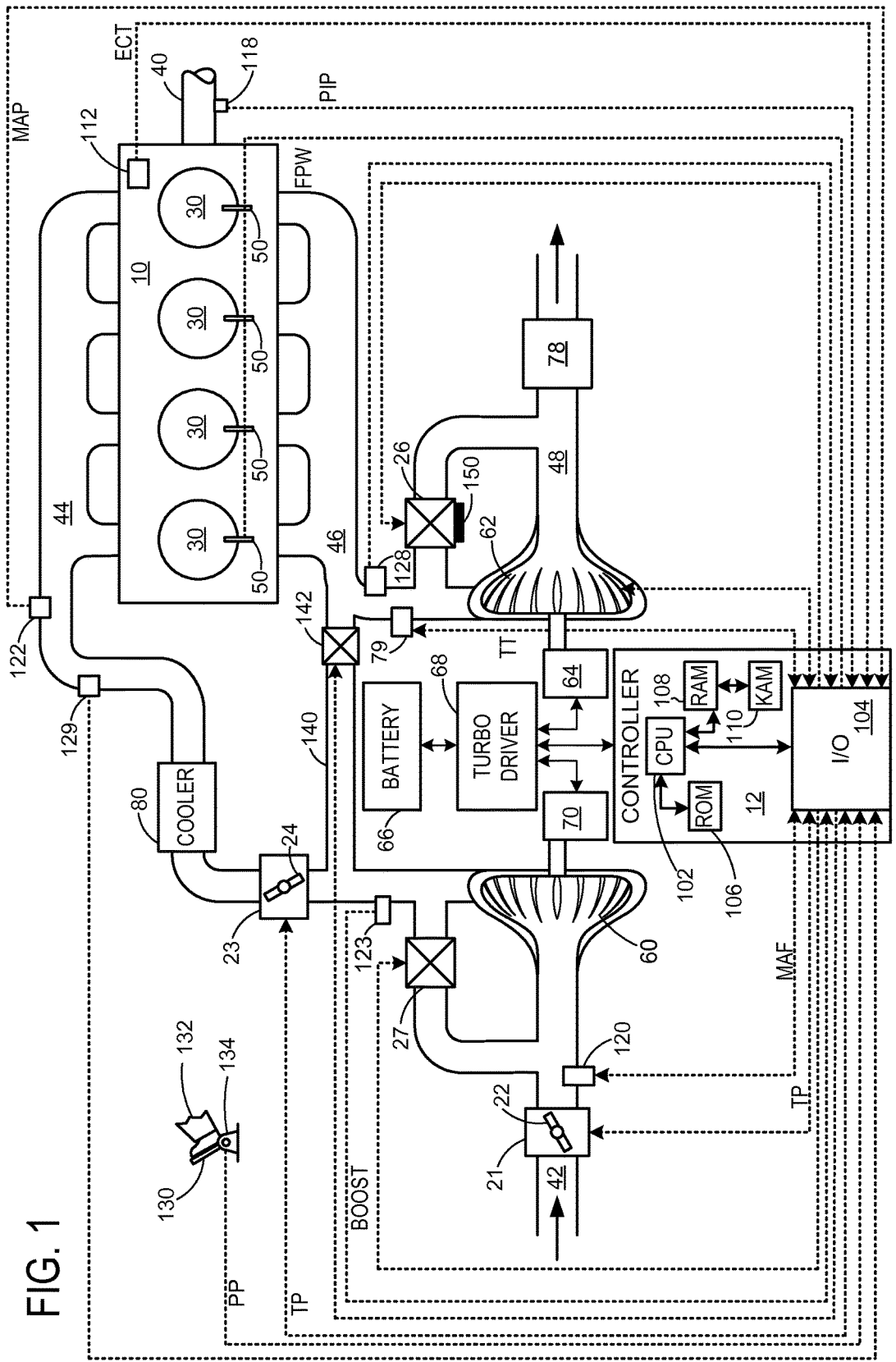
FIG. 1 is a schematic diagram showing an example engine.
Figure 2:
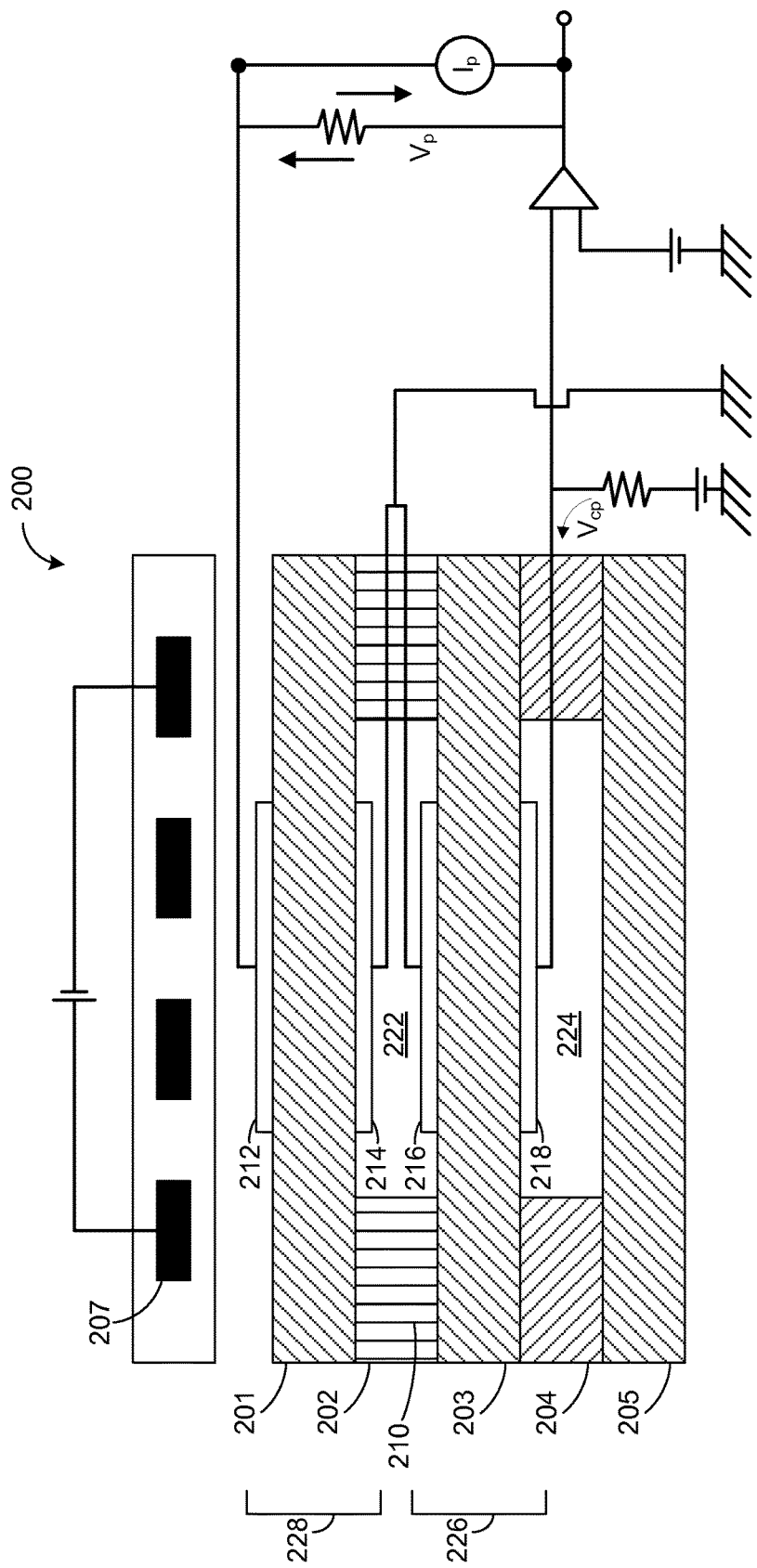
FIG. 2 shows a schematic diagram of an example oxygen sensor.
Figure 3:
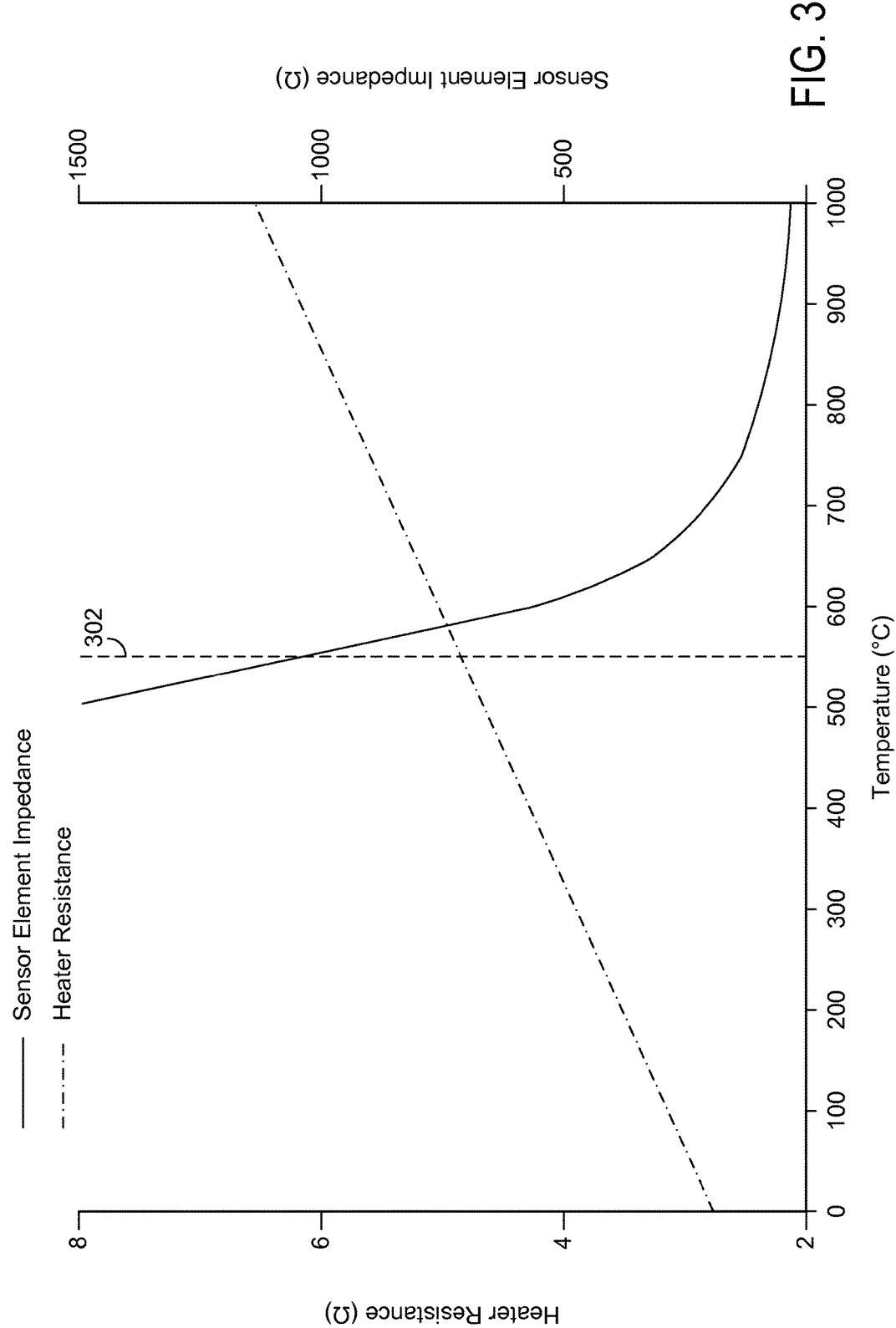
FIG. 3 shows heater resistance and sensor element impedance both as a function of temperature for an example oxygen sensor.
Figure 4:
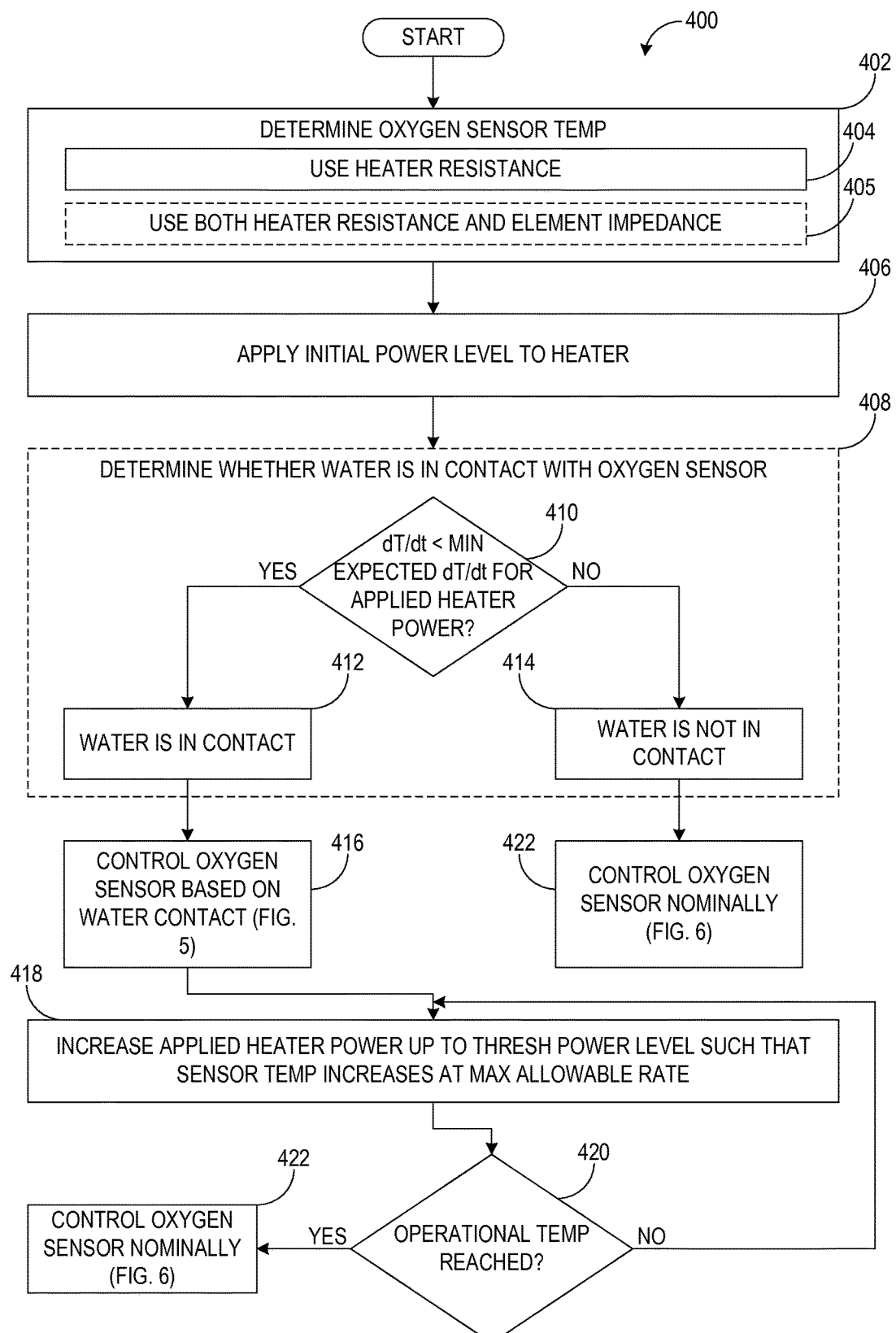
FIG. 4 shows a flowchart illustrating a method of controlling an oxygen sensor.
Figure 5:
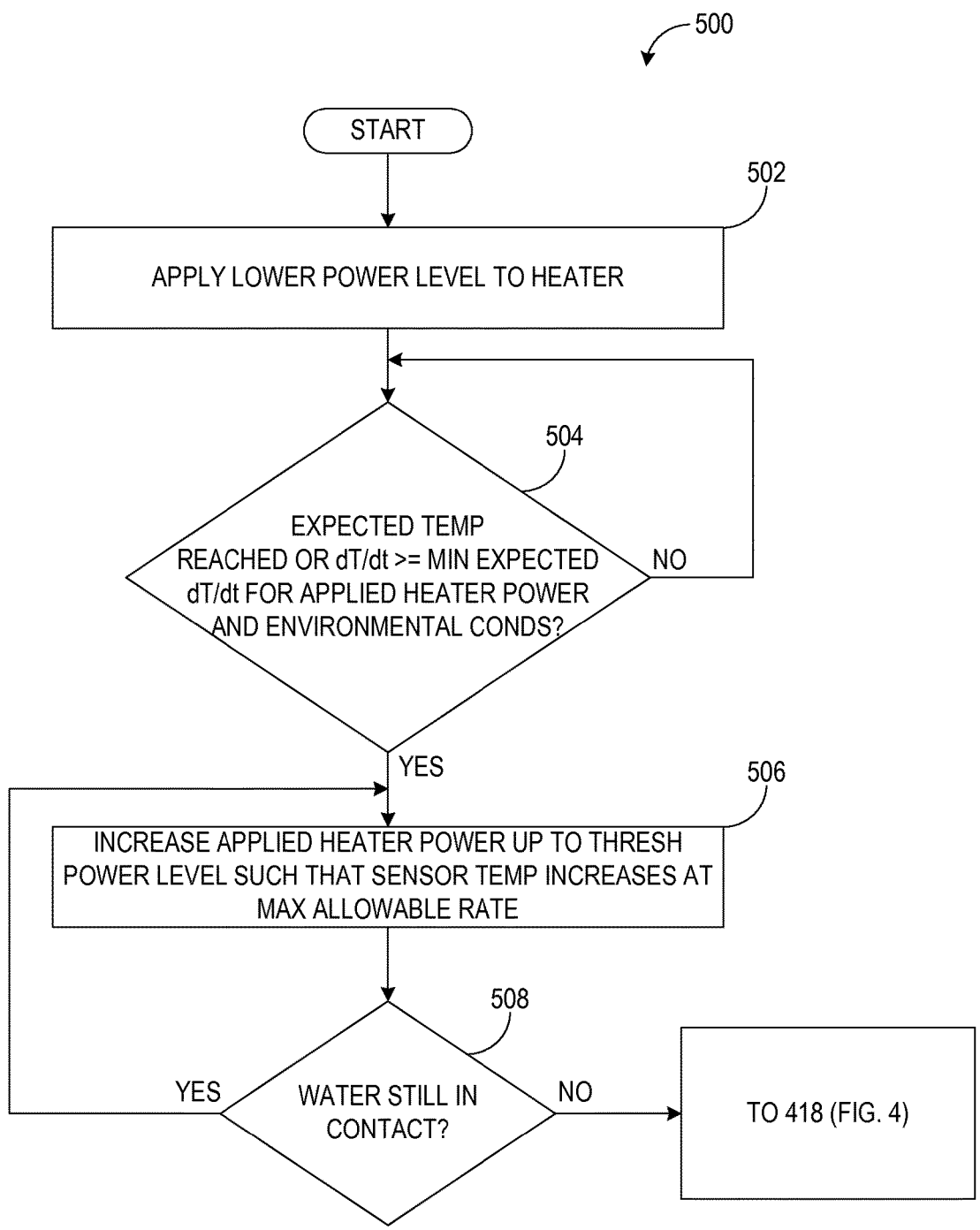
FIG. 5 shows a flowchart illustrating a method of controlling an oxygen sensor based on water contact with the sensor.
Figure 6:
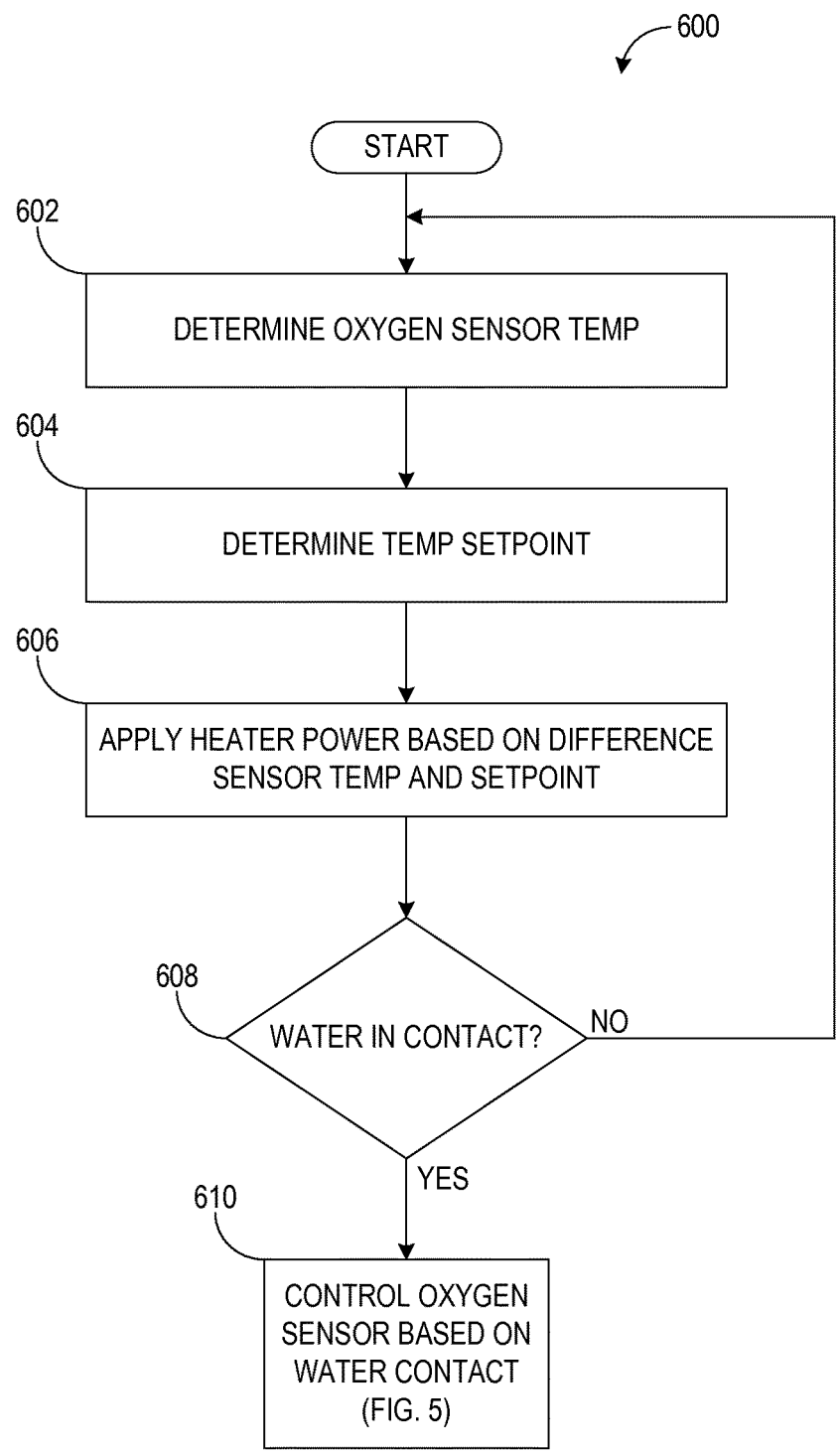
FIG. 6 shows a flowchart illustrating a method of nominally controlling an oxygen sensor.
Figure 7:
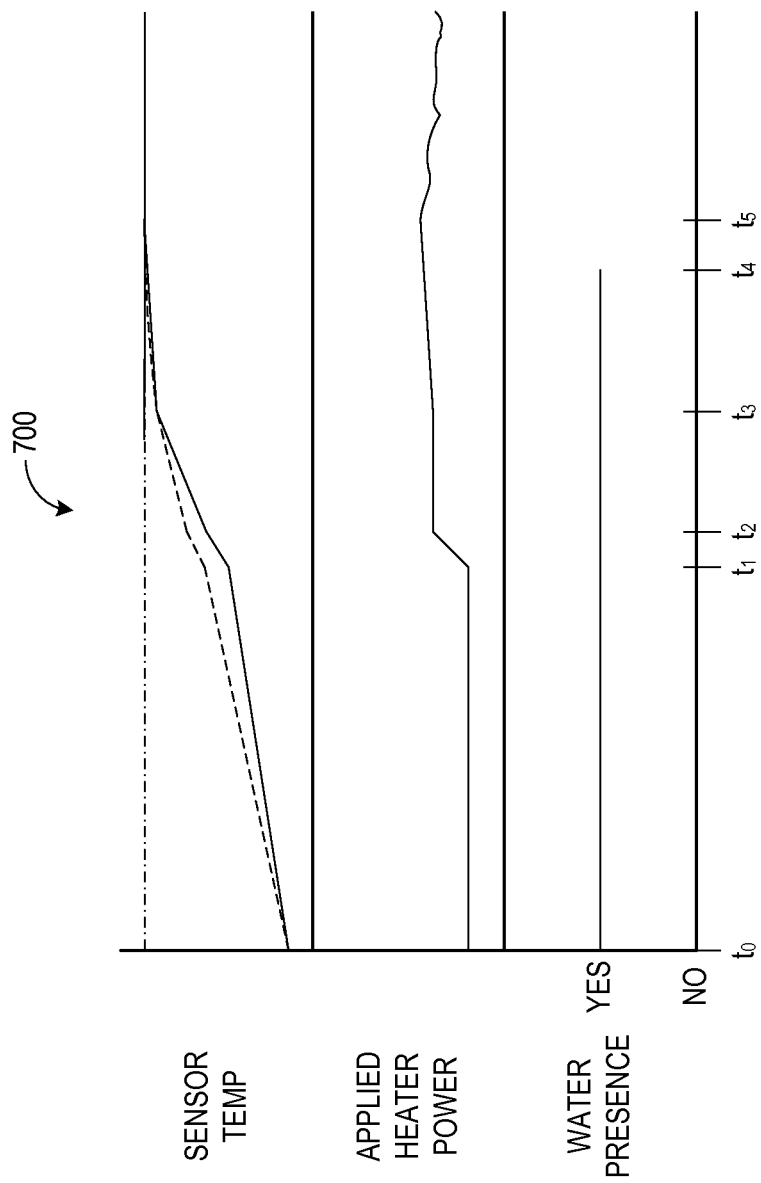
FIG. 7 shows a graph illustrating operation of an example oxygen sensor.

Various methods for operating an oxygen sensor are provided. In one example, a method of operating an oxygen sensor comprises applying power to a heater of the oxygen sensor, and indicating whether water is in contact with the oxygen sensor based on a time rate of change of a temperature of the oxygen sensor. FIG. 1 is a schematic diagram showing an example engine, FIG. 2 shows a schematic diagram of an example oxygen sensor, FIG. 3 shows heater resistance and sensor element impedance both as a function of temperature for an example oxygen sensor, FIG. 4 shows a flowchart illustrating a method of controlling an oxygen sensor, FIG. 5 shows a flowchart illustrating a method of controlling an oxygen sensor based on water contact with the sensor, FIG. 6 shows a flowchart illustrating a method of nominally controlling an oxygen sensor, and FIG. 7 shows a graph illustrating operation of an example oxygen sensor. The engine of FIG. 1 also includes a controller configured to carry out the methods depicted in FIGS. 4-6.

FIG. 1 is a schematic diagram showing an example engine 10, which may be included in a propulsion system of an automobile. The engine 10 is shown with four cylinders 30. However, other numbers of cylinders may be used in accordance with the current disclosure. Engine 10 may be controlled at least partially by a control system including controller 12, and by input from a vehicle operator 132 via an input device 130. In this example, input device 130 includes an accelerator pedal and a pedal position sensor 134 for generating a proportional pedal position signal PP. Each combustion chamber (e.g., cylinder) 30 of engine 10 may include combustion chamber walls with a piston (not shown) positioned therein. The pistons may be coupled to a crankshaft 40 so that reciprocating motion of the piston is translated into rotational motion of the crankshaft. Crankshaft 40 may be coupled to at least one drive wheel of a vehicle via an intermediate transmission system (not shown). Further, a starter motor may be coupled to crankshaft 40 via a flywheel to enable a starting operation of engine 10.

Combustion chambers 30 may receive intake air from intake manifold 44 via intake passage 42 and may exhaust combustion gasses via exhaust passage 48. Intake manifold 44 and exhaust manifold 46 can selectively communicate with combustion chamber 30 via respective intake valves and exhaust valves (not shown). In some embodiments, combustion chamber 30 may include two or more intake valves and/or two or more exhaust valves.

Fuel injectors 50 are shown coupled directly to combustion chamber 30 for injecting fuel directly therein in proportion to the pulse width of signal FPW received from controller 12. In this manner, fuel injector 50 provides what is known as direct injection of fuel into combustion chamber 30. The fuel injector may be mounted in the side of the combustion chamber or in the top of the combustion chamber, for example. Fuel may be delivered to fuel injector 50 by a fuel system (not shown) including a fuel tank, a fuel pump, and a fuel rail. In some embodiments, combustion chambers 30 may alternatively, or additionally, include a fuel injector arranged in intake manifold 44 in a configuration that provides what is known as port injection of fuel into the intake port upstream from each combustion chamber 30.

Intake passage 42 may include throttle 21 and 23 having throttle plates 22 and 24, respectively. In this particular example, the position of throttle plates 22 and 24 may be varied by controller 12 via signals provided to an actuator included with throttles 21 and 23. In one example, the actuators may be electric actuators (e.g., electric motors), a configuration that is commonly referred to as electronic throttle control (ETC). In this manner, throttles 21 and 23 may be operated to vary the intake air provided to combustion chamber 30 among other engine cylinders. The position of throttle plates 22 and 24 may be provided to controller 12 by throttle position signal TP. Intake passage 42 may further include a mass air flow sensor 120, a manifold air pressure sensor 122, and a throttle inlet pressure sensor 123 for providing respective signals MAF (mass airflow) MAP (manifold air pressure) to controller 12.

Exhaust passage 48 may receive exhaust gasses from cylinders 30. Exhaust gas sensor 128 is shown coupled to exhaust passage 48 upstream of turbine 62 and emission control device 78. Sensor 128 may be selected from among various suitable sensors for providing an indication of exhaust gas air/fuel ratio such as a linear oxygen sensor or UEGO (universal or wide-range exhaust gas oxygen), a two-state oxygen sensor or EGO, a $NO_x$, HC, or CO sensor, for example. Emission control device 78 may be a three way catalyst (TWC), NOx trap, various other emission control devices, or combinations thereof.

FIG. 1 also illustrates the inclusion of an intake air sensor 129 coupled to intake passage 42. Sensor 129 may be any suitable sensor for providing an indication of intake air oxygen content such as a linear oxygen sensor or UEGO (universal or wide-range exhaust gas oxygen), a two-state oxygen sensor or EGO, a HEGO (heated EGO), a $NO_x$, HC, or CO sensor, for example. In some implementations, both sensor 128 and sensor 129 may be included in engine 10 as shown in FIG. 1, while in other implementations one and not the other of sensors 128 and 129 may be included.

Exhaust temperature may be measured by one or more temperature sensors (not shown) located in exhaust passage 48. Alternatively, exhaust temperature may be inferred based on engine operating conditions such as speed, load, AFR, spark retard, etc.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112, shown schematically in one location within the engine 10; a profile ignition pickup signal (PIP) from Hall effect sensor 118 (or other type) coupled to crankshaft 40; the throttle position (TP) from a throttle position sensor, as discussed; and absolute manifold pressure signal, MAP, from sensor 122, as discussed. Engine speed signal, RPM, may be generated by controller 12 from signal PIP. Manifold pressure signal MAP from a manifold pressure sensor may be used to provide an indication of vacuum, or pressure, in the intake manifold 44. Note that various combinations of the above sensors may be used, such as a MAF sensor without a MAP sensor, or vice versa. During stoichiometric operation, the MAP sensor can give an indication of engine torque. Further, this sensor, along with the detected engine speed, can provide an estimate of charge (including air) inducted into the cylinder. In one example, sensor 118, which is also used as an engine speed sensor, may produce a predetermined number of equally spaced pulses every revolution of the crankshaft 40. In some examples, storage medium read-only memory 106 may be programmed with computer readable data representing instructions executable by processor 102 for performing the methods described below as well as other variants that are anticipated but not specifically listed.

Engine 10 may further include a compression device such as a turbocharger or supercharger including at least a compressor 60 arranged along intake manifold 44. For a turbocharger, compressor 60 may be at least partially driven by a turbine 62, via, for example a shaft, or other coupling arrangement. The turbine 62 may be arranged along exhaust passage 48 and communicate with exhaust gasses flowing therethrough. Various arrangements may be provided to drive the compressor. For a supercharger, compressor 60 may be at least partially driven by the engine and/or an electric machine, and may not include a turbine. Thus, the amount of compression provided to one or more cylinders of the engine via a turbocharger or supercharger may be varied by controller 12. In some cases, the turbine 62 may drive, for example, an electric generator 64, to provide power to a battery 66 via a turbo driver 68. Power from the battery 66 may then be used to drive the compressor 60 via a motor 70. Further, a sensor 123 may be disposed in intake manifold 44 for providing a BOOST signal to controller 12.

Further, exhaust passage 48 may include wastegate 26 for diverting exhaust gas away from turbine 62. In some embodiments, wastegate 26 may be a multi-staged wastegate, such as a two-staged wastegate with a first stage configured to control boost pressure and a second stage configured to increase heat flux to emission control device 78. Wastegate 26 may be operated with an actuator 150, which may be an electric actuator such as an electric motor, for example, though pneumatic actuators are also contemplated. Intake passage 42 may include a compressor bypass valve 27 configured to divert intake air around compressor 60. Wastegate 26 and/or compressor bypass valve 27 may be controlled by controller 12 via actuators (e.g., actuator 150) to be opened when a lower boost pressure is desired, for example.

Intake passage 42 may further include charge air cooler (CAC) 80 (e.g., an intercooler) to decrease the temperature of the turbocharged or supercharged intake gasses. In some embodiments, charge air cooler 80 may be an air to air heat exchanger. In other embodiments, charge air cooler 80 may be an air to liquid heat exchanger.

Further, in the disclosed embodiments, an exhaust gas recirculation (EGR) system may route a desired portion of exhaust gas from exhaust passage 48 to intake passage 42 via EGR passage 140. The amount of EGR provided to intake passage 42 may be varied by controller 12 via EGR valve 142. Further, an EGR sensor (not shown) may be arranged within the EGR passage and may provide an indication of one or more of pressure, temperature, and concentration of the exhaust gas. Alternatively, the EGR may be controlled through a calculated value based on signals from the MAF sensor (upstream), MAP (intake manifold), MAT (manifold gas temperature) and the crank speed sensor. Further, the EGR may be controlled based on an exhaust $O_2$ sensor and/or an intake oxygen sensor (intake manifold).

For example, the EGR dilution percentage of the intake charge at a given time (e.g., the proportion of combusted gases to air in an intake passage of the engine) may be inferred from the output of the intake air sensor 129 (e.g., intake oxygen sensor). In particular, when oxygen intake concentration is reduced, an increase in EGR may be inferred since the presence of EGR may dilute oxygen in the intake stream at the intake air sensor 129. Conversely, when oxygen intake concentration increases, a decrease in EGR may be inferred due to a reduction of EGR. Controller 12 may estimate the percent dilution of the EGR flow based on feedback from intake air sensor 129. Further, the controller 12 may then estimate an EGR amount or EGR flow rate based on feedback from the intake air sensor 129. In some examples, the controller 12 may then adjust one or more of the EGR valve 142, throttle 23, compressor bypass valve 27, and wastegate 26 to achieve a desired EGR dilution percentage of the intake charge and/or desired EGR flow rate.

Under some conditions, the EGR system may be used to regulate the temperature of the air and fuel mixture within the combustion chamber. FIG. 1 shows a high pressure EGR system where EGR is routed from upstream of a turbine of a turbocharger to downstream of a compressor of a turbocharger. In other embodiments, the engine may additionally or alternatively include a low pressure EGR system where EGR is routed from downstream of a turbine of a turbocharger to upstream of a compressor of the turbocharger.

FIG. 2 shows a schematic view of an example embodiment of an oxygen sensor 200 configured to measure a concentration of oxygen ($O_2$) in an intake airflow in an intake passage or an exhaust gas stream in an exhaust passage. In some examples, the sensor 200 may be a UEGO sensor. The sensor 200 may thus correspond to one or both of sensors 128 and 129 of FIG. 1, for example. It will be appreciated, however, that sensors 128 and 129 may deviate in some respects from the sensor 200—for example, they may employ one or more modifications.

As shown in FIG. 2, the sensor 200 comprises a plurality of layers of one or more ceramic materials arranged in a stacked configuration. In the embodiment of FIG. 2, five ceramic layers are depicted as layers 201, 202, 203, 204, and 205. These layers include one or more layers of a solid electrolyte capable of conducting ionic oxygen. Examples of suitable solid electrolytes include, but are not limited to, zirconium oxide-based materials. Further, in some embodiments, a heater 207 may be disposed in thermal communication with the layers to increase the ionic conductivity of the layers. While the depicted oxygen sensor is formed from five ceramic layers, it will be appreciated that the oxygen sensor may include other suitable numbers of ceramic layers.

The layer 202 includes a material or materials creating a diffusion path 210. The diffusion path 210 is configured to introduce gasses into a first internal cavity 222 via diffusion. The diffusion path 210 may be configured to allow one or more components of intake air or exhaust gasses, including but not limited to a desired analyte (e.g., $O_2$), to diffuse into internal cavity 222 at a more limiting rate than the analyte can be pumped in or out by a pumping electrodes pair 212 and 214. In this manner, a stoichiometric level of $O_2$ may be obtained in the first internal cavity 222.

The sensor 200 further includes a second internal cavity 224 within the layer 204 separated from the first internal cavity 222 by the layer 203. The second internal cavity 224 is configured to maintain a constant oxygen partial pressure equivalent to a stoichiometric condition; e.g., an oxygen level present in the second internal cavity 224 is equal to that which the intake air or exhaust gas would have if the air-fuel ratio were stoichiometric. The oxygen concentration in the second internal cavity 224 is held constant by pumping voltage $V_{cp}$. Herein, the second internal cavity 224 may be referred to as a reference cell.

A pair of sensing electrodes 216 and 218 is disposed in communication with the first internal cavity 222 and the reference cell 224. The sensing electrodes pair 216 and 218 detects a concentration gradient that may develop between the first internal cavity 222 and the reference cell 224 due to an oxygen concentration in the intake air or exhaust gas that is higher than or lower than the stoichiometric level. A high oxygen concentration may be caused by a lean intake air or exhaust gas mixture, while a low oxygen concentration may be caused by a rich mixture.

A pair of pumping electrodes 212 and 214 is disposed in communication with the internal cavity 222, and is configured to electrochemically pump a selected gas constituent (e.g., $O_2$) from internal cavity 222 through layer 201 and out of the sensor 200. Alternatively, the pair of pumping electrodes 212 and 214 may be configured to electrochemically pump a selected gas through layer 201 and into internal cavity 222. Herein, the pumping electrodes pair 212 and 214 may be referred to as an $O_2$ pumping cell.

The electrodes 212, 214, 216, and 218 may be made of various suitable materials. In some embodiments, the electrodes 212, 214, 216, and 218 may be at least partially made of a material that catalyzes the dissociation of molecular oxygen. Examples of such materials include, but are not limited to, electrodes containing platinum and/or silver.

The process of electrochemically pumping the oxygen out of or into the internal cavity 222 includes applying a voltage $V_p$ across the pumping electrode pair 212 and 214. The pumping voltage $V_p$ applied to the $O_2$ pumping cell pumps oxygen into or out of the first internal cavity 222 in order to maintain a stoichiometric level of oxygen in the cavity pumping cell. The resulting pumping current $I_p$ is proportional to the concentration of oxygen in the exhaust gas. A suitable control system (not shown in FIG. 2) generates the pumping current signal $I_p$ as a function of the intensity of the applied pumping voltage $V_p$ required to maintain a stoichiometric level within the first internal cavity 222. Thus, a lean mixture will cause oxygen to be pumped out of the internal cavity 222 and a rich mixture will cause oxygen to be pumped into the internal cavity 222.

It should be appreciated that the oxygen sensor described herein is merely an example embodiment of an oxygen sensor, and that other embodiments of oxygen sensors may have additional and/or alternative features and/or designs.

It is well known that the conductivity of a material changes with temperature. For an oxygen ionic conducting electrolyte such as zirconia, the ionic conductivity typically increases as the temperature increases. Other factors such as impurities, grain boundaries, structure, and geometry can affect the conductivity of the zirconia. For a fixed geometry and structure, the impedance (which is the inverse of the conductivity) of a zirconia element is directly related to the temperature of the element. Thus, the temperature of an oxygen sensor element may be determined by measuring the impedance of the oxygen sensor element. The oxygen sensor element impedance may be measured by measuring the voltage drop across the oxygen sensor element (e.g., by using an AC technique). For oxygen sensor 200, the sensor element impedance may be specifically measured across either sensing cell 226, which comprises layer 203 and electrodes 216 and 218, or pumping cell 228, which comprises layer 201 and electrodes 212 and 214, for example. In this approach, impedance measurement of a cell may be based on the applied voltage and resulting current associated with that cell—e.g., the impedance of pumping cell 228 may be determined based on the pumping voltage $V_p$ applied to the pumping cell and the resulting pumping current $I_p$. The impedance of sensing cell 226 may be analogously determined based on the pumping voltage applied to the sensing cell and the resulting pumping current.

In some approaches, the impedance of an oxygen sensor is used to control the temperature of the oxygen sensor. Since, as described above, the impedance of an oxygen sensor element can be used as an indication of the temperature of the sensor element, the impedance of the sensor element may be measured in real time and used to control its temperature—e.g., the output of a heater such as heater 207 may be controlled in closed loop fashion to minimize the difference between a desired sensor element impedance and an actual (e.g., measured) sensor element impedance, and thus to minimize the difference between a desired sensor temperature and an actual sensor temperature. In this way, the oxygen sensor may be imbued with the desired sensor temperature by controlling heater output according to impedance.

The impedance of some oxygen sensor elements (e.g., concentration cells), however, increases (e.g., exponentially) as sensor element temperature decreases. At temperatures less than and equal to a threshold temperature, the oxygen sensor element impedance may be prohibitively high for measurement. As such, the oxygen sensor temperature cannot be determined at and below the threshold temperature via impedance measurement. In some configurations, the threshold temperature may be frequently undershot—for example, the temperature of an oxygen sensor (e.g., sensor 200) configured to perform sensing in a motor vehicle may be below the threshold temperature upon cold start of an associated engine (e.g., engine 10 of FIG. 1). Such cold starts may occur on a regular basis. Consequently, the temperature of an oxygen sensor may be unavailable for significant portions of a vehicle's life, which may lead to increased emissions and undesired engine operation.

Accordingly, temperature measurement of oxygen sensor 200 may utilize other data in addition to or in lieu of impedance, depending on various operating conditions. For example, the resistance of heater 207 may be used to assess the temperature of oxygen sensor 200. In some examples, heater 207 may be comprised of a material (e.g., platinum) whose resistance is directly proportional to its temperature. Since the temperature of heater 207 correlates to the temperature of oxygen sensor 200, the heater temperature may be used to assess temperature of the overall oxygen sensor. Moreover, the heater temperature may be sufficiently measured over a relatively wide range of temperatures (e.g., from −273.15° C. to greater than 900° C.), including temperatures below the threshold temperature at and below which impedance measurement of an oxygen sensor element may no longer be feasible. Accordingly, the measured temperature of heater 207 (e.g., determined by measuring the resistance of the heater) may be used to determine the temperature of oxygen sensor 200 at and below the threshold temperature (e.g., 550° C.). Above the threshold temperature, the oxygen sensor element impedance (e.g., the impedance of sensing cell 226 or pumping cell 228) may be used to determine the temperature of oxygen sensor 200. In some examples, both the heater resistance and sensor element impedance may be used above the threshold temperature.

The heater resistance and sensor element impedance may be combined in various suitable manners to determine the temperature of oxygen sensor 200—e.g., a weighted average of the two quantities may be computed, with the sensor temperature determined based on the weighted average. In some examples, one or both of the heater resistance and sensor element impedance may be selected and potentially combined based on predetermined knowledge that one parameter is more accurate than the other in a range of temperatures. For example, oxygen sensor temperature may be preferentially determined based on heater resistance for a range of temperatures in which it is known that heater resistance temperature measurement yields readings with reduced tolerance and greater accuracy than those obtained from sensor element impedance. This range of temperatures may be a first, lower range of temperatures including engine cold start temperatures to 550° C., for example. Similarly, oxygen sensor temperature may be preferentially determined based on sensor element impedance for a range of temperatures in which it is known that impedance temperature measurement yields readings with greater accuracy than those obtained from heater resistance. This range of temperatures may be a second, higher range of temperatures including temperatures extending from 550° C. to a maximum operational temperature of an engine.

Since the resistance of heater 207 correlates to the temperature of oxygen sensor 200 below, at, and above the threshold temperature, the heater resistance may be used to persistently determine the temperature of the oxygen sensor throughout the duration of sensor operation. If the resistance of heater 207 indicates a temperature at or below the threshold temperature, this resistance alone may be used to determine the temperature of oxygen sensor 200. If, conversely, the resistance of heater 207 indicates a temperature above the threshold temperature, an impedance measurement of an oxygen sensor element may be subsequently performed, with both the measured resistance and impedance being used to determine the temperature of oxygen sensor 200 as described above.

FIG. 3 shows heater resistance and sensor element impedance both as a function of temperature for an example oxygen sensor. The example oxygen sensor may correspond to one or more of oxygen sensor 128, 129, and 200. The heater resistance may be the heater resistance of heater 207, while the sensor element impedance may be the impedance of pumping cell 228, for example. In the depicted example, the heater resistance correlates with temperature as a linear function, and as such the heater resistance can be used to determine the temperature of the oxygen sensor. The sensor element impedance, however, decreases exponentially as a function of temperature. At temperatures below and equal to a threshold temperature 302 (e.g., 550° C.), the sensor element impedance is prohibitively high for measurement and as such cannot be used to determine the temperature of the oxygen sensor. At temperatures above threshold temperature 302, however, the sensor element impedance becomes sufficiently low (e.g., 1050Ω) for measurement and oxygen sensor temperature determination. Consequently, determination of the temperature of the oxygen sensor may utilize the heater resistance and not the sensor element impedance at or below threshold temperature 302, but may use both the heater resistance and the sensor element impedance above the threshold temperature.

By using heater resistance and selectively employing oxygen sensor element impedance in this way, the temperature of oxygen sensor 200 may be known for a greater portion, and in some examples during the entirety, of sensor (and in some examples engine) operation, relative to other approaches. This may increase the duration in which oxygen sensor 200 is nominally controlled (e.g., in closed loop fashion) and decrease the time taken to initiate nominal oxygen sensor control, in turn increasing the overall accuracy of oxygen sensor control, reducing engine emissions, and increasing fuel economy.

As described above, the temperature of oxygen sensor 200 may be controlled by controlling the output (e.g., heating) of heater 207. The heater 207 may be controlled in part based on a desired oxygen sensor temperature; the temperature of oxygen sensor 200 may be measured in the manners described above and the heater controlled to minimize the difference between the measured and desired oxygen sensor temperatures. Heater 207 may also be controlled according to the presence of water—e.g., the heater may be controlled differently depending on whether or not water in contact with oxygen sensor 200 is detected. Heating by heater 207 may be altered in this manner to prevent cracking that might otherwise occur in oxygen sensor 200 as a result of heating the sensor nominally when water is in contact with the sensor. Without altering heater operation according to water presence, an oxygen sensor may be heated by applying nominal power levels to the heater that may cause thermal shock to the sensor due to water contact; the nominal power levels are excessive for heating in the presence of water contact but are appropriate for heating in the absence of water contact. Such thermal shock may result in cracks in the oxygen sensor, degrading its sensing capabilities and thus engine operation.

In some approaches, thermal shock and cracking in an oxygen sensor is avoided by controlling a heater of the sensor according to a dew point temperature. Here, the temperature of exhaust gas is monitored to determine when it reaches the dew point temperature, which is a predetermined temperature at which it is inferred that water in the exhaust gas is evaporated. Under some conditions, however, unevaporated water may nevertheless remain in contact with the oxygen sensor even upon reaching the dew point temperature—for example, puddled water accumulated on the oxygen sensor may remain. Alternatively or additionally, unevaporated water may remain in the exhaust gas and/or generally in the exhaust system. Moreover, even if water on the sensor was evaporated upon reaching the dew point temperature, additional water may subsequently come into contact with the sensor (e.g., due to a water splash). This is exacerbated in some approaches by the application of maximum power to the oxygen sensor heater, as in these approaches the maximum power may be applied until the oxygen sensor reaches its operational (e.g., desired) temperature; in the presence of water contact, the maximum power is applied for an extended duration due to the time taken to evaporate the water. Extended application of maximum power to the oxygen sensor heater may also cause cracks leading to sensor degradation. Once the operational temperature of the oxygen sensor is reached, the sensor temperature may be controlled according to closed loop control. Such closed loop control, however, may cause a near immediate increase in heater power to the maximum power in response to water splash against the oxygen sensor. This immediate increase to the maximum power, in addition its sustained application, may cause cracks in the sensor and thus sensor degradation.

Some approaches attempt to detect water impingement against an oxygen sensor based on pumping current. While this may be suitable for some oxygen sensor configurations, it may be unsuitable for other configurations—for example, pumping current may be used to detect water impingement for an oxygen sensor positioned in an engine intake system, due to the presence of oxygen in intake air, but not for an oxygen sensor positioned in an engine exhaust system, due to the lack of oxygen in exhaust gas. The pumping current associated with an oxygen sensor positioned in the exhaust system may remain around zero even in the event of water impingement. This minimal change in pumping current may be insufficient to detect water impingement. While in some approaches the voltage applied to an oxygen sensor element (e.g., pumping cell 228) may be varied (e.g., to dissociate oxygen from other compounds), this voltage is typically varied only for small durations under specific conditions, both of which are unsuitable for detecting oxygen sensor water impingement.

Accordingly, the present disclosure provides mechanisms for detecting water impingement on oxygen sensor 200 in real time based on changes in the temperature of the oxygen sensor and the power applied to heater 207. Mechanisms for appropriate operating oxygen sensor 200 and heater 207 in the presence of water contact on the sensor are further provided.

To detect water impingement on oxygen sensor 200, the time rate of change of the temperature of the oxygen sensor may be determined (e.g., based on two or more oxygen sensor temperatures determined as described herein) and compared to a minimum time rate of change of the oxygen sensor temperature that is expected for the power being applied to heater 207. If the determined time rate of change of the oxygen sensor temperature is less than the minimum expected time rate of change for the applied heater power, it may be determined that water is in contact with oxygen sensor 200. Various suitable approaches may be employed for determining the minimum expected time rate of change for the applied heater power. For example, a lookup table storing minimum expected time rates of change of oxygen sensor temperature associated with heater power levels may be accessed; a particular minimum expected time rate of change may be retrieved by accessing the lookup table with the power being applied to heater 207. Minimum expected time rates of change of oxygen sensor temperature may be determined offline in a testing environment, for example, and used to populate the lookup table.

If water impingement on oxygen sensor 200 is detected, a relatively reduced power level may be applied to heater 207 that is determined to be acceptable for heating the sensor even in the presence of water contact. The reduced power level may be reduced relative to power levels applied to heater 207 during nominal control of oxygen sensor 200—e.g., when water is determined to not be in contact with the sensor. Nominal control of oxygen sensor 200 may include closed loop control based on a desired temperature as described in further detail below. After applying the relatively reduced power level to heater 207, a determination may be made as to whether the expected temperature of oxygen sensor 200 for the power being applied to the heater has been reached (which may include accessing a suitable data structure such as a lookup table storing expected oxygen sensor temperatures associated with heater power levels), and/or whether the time rate of change of the oxygen sensor temperature is greater than or equal to the expected time rate of change of the oxygen sensor temperature for the applied heater power (e.g., by accessing a lookup table as described above). The expected temperature of oxygen sensor 200 may also be a temperature expected for various environmental conditions, including but not limited to intake airflow, exhaust temperature, etc. As such, one or more of these environmental conditions may be determined prior to considering the expected oxygen sensor temperature.

Once one or both of expected oxygen sensor temperature and time rate of change of oxygen sensor temperature conditions are met, the power being applied to heater 207 may be increased up to a threshold power level such that the oxygen sensor temperature increases at (e.g., up to) a maximum allowable rate. The maximum allowable rate may be selected to avoid immediate or unacceptably rapid increases that may degrade oxygen sensor 200, and the threshold power level may be less than a maximum power level that may be applied to heater 207; this maximum power level may be the power level applied to the heater when heating the oxygen sensor to achieve a desired oxygen sensor temperature when it is determined that water is not in contact with the sensor, for example. A determination as to whether water is still in contact with oxygen sensor 200 may then be made. If water is determined to still be in contact with oxygen sensor 200, the power applied to heater 207 may be continually increased as long as water contact on the sensor is detected. More specifically, the heater power may be continually increased as long as water contact on oxygen sensor 200 is detected if a relatively small quantity of water is in contact with the sensor and the temperature of the sensor is increasing at the minimum expected rate. The quantity of water may be estimated based on the temperature and/or time rate of change of the temperature of oxygen sensor 200; for example, a relatively greater quantity of water in contact with the sensor may be inferred if the time rate of change of sensor temperature falls below an expected time rate of change of sensor temperature by a relatively large margin. If water is not determined to be in contact with oxygen sensor 200, the power being applied to heater 207 may be increased up to the threshold power level as described above. Once a desired or operational temperature of oxygen sensor 200 is reached—e.g., a temperature at which the oxygen sensor provides desired sensing—nominal control of the oxygen sensor may be applied, which may include closed loop control. Closed loop control may control the power supplied to heater 207 to minimize the difference between the temperature of oxygen sensor 200 and the desired or operational temperature, for example. The presence of water contact on oxygen sensor 200 may be persistently evaluated during nominal oxygen sensor control, however, with detection of water contact on the sensor prompting the control described herein used to operate the oxygen sensor and heater 207 in the presence of water contact.

The approaches described herein allows the temperature of oxygen sensor 200 to be determined upon engine startup as well as the presence of water contact on the sensor. Oxygen sensor 200 may be appropriate controlled in the presence of water contact so as to avoid actions that may degrade the sensor, such as immediate increases in heater power and sustained application of maximum heater power. This may in turn extend the operational life of oxygen sensor 200. The time taken to reach the operational temperature (e.g., light-off temperature) of oxygen sensor 200 may be reduced as well, which may increase fuel economy and drivability, and reduce engine emissions. Moreover, the approaches described herein may maximize the rate at which oxygen sensor 200 returns to its operational temperature after water contact occurs—particularly water contact occurring after the oxygen sensor initially reached its operational temperature.

FIG. 4 shows a flowchart illustrating a method 400 of controlling an oxygen sensor. Method 400 may be employed to control one or more of oxygen sensors 128, 129, and 200, for example. Method 400 may be stored as machine-readable instructions on ROM 106 executable by CPU 102, both of controller 12 of FIG. 1, for example. In some examples, method 400 includes determining whether water is in contact with the oxygen sensor, controlling the oxygen sensor according to a first control scheme if water is in contact with the sensor, and controlling the oxygen sensor according to a second control scheme different than the first control scheme if water is not in contact with the sensor.

At 402 of method 400, the temperature of the oxygen sensor is determined. Determining the temperature of the oxygen sensor includes, at 404, using the resistance of a heater (e.g., heater 207 of FIG. 2) of the oxygen sensor in determining the oxygen sensor temperature. As described above, the impedance of an oxygen sensor element (e.g., sensing cell 226 or pumping cell 228 of FIG. 2) of the oxygen sensor may be unsuitably high for determining the oxygen sensor temperature at and below a threshold temperature. The heater resistance, however, may directly correlate with the oxygen sensor temperature throughout its range of operating temperatures. As such, the heater resistance and not the sensor element impedance may be used at and below the threshold temperature, while both the heater resistance and the sensor element impedance may be used above the threshold temperature. Accordingly, determining the temperature of the oxygen sensor includes, at 405, optionally using both the heater resistance and sensor element impedance in determining the oxygen sensor temperature. Thus, in some examples a measurement of heater resistance may be followed by a measurement of sensor element impedance, and both the heater resistance and sensor element impedance may be used to determine the oxygen sensor temperature. Using both the heater resistance and sensor element impedance may include weighting and averaging the resistance and impedance, for example.

At 406 of method 400, an initial power level is applied to the oxygen sensor heater. The initial power level may be a relatively low or reduced, and in some examples minimum, power level that drives heating of the oxygen sensor but is not high enough to cause thermal shock to the sensor and cracking that otherwise might occur in the presence of water contacting the sensor while applying power greater than the initial power level. More specifically, the initial power level may be sufficiently high enough to cause the temperature of the oxygen sensor to change at a minimum desired rate (even in the presence of water contact with the sensor) so that the time rate of change of the oxygen sensor temperature can be evaluated to determine whether water is in contact with the sensor. Further, the initial power level may be reduced relative to power levels employed during nominal control of the oxygen sensor, described in further detail below.

At 408 of method 400, it is determined whether water is in contact with the oxygen sensor. Determining whether water is in contact with the oxygen sensor may include, at 410, determining whether the time rate of change of the oxygen sensor temperature (dT/dt) is less than a minimum expected time rate of change of the oxygen sensor temperature ($dT_{ex}$) expected for the power level being applied to the heater (e.g., the initial power level). A minimum expected time rate of change of the oxygen sensor temperature may be determined by accessing a data structure such as a lookup table storing minimum expected time rates of oxygen sensor temperature change associated with heater power levels, for example. In some examples, dT/dt may be used to infer the quantity of water in contact with the oxygen sensor; for example, if dT/dt falls below $dT_{ex}$ by a relatively large margin, a relatively large quantity of water may be inferred, whereas if dT/dt falls below $dT_{ex}$ by a relatively small margin, a relatively small quantity of water may be inferred. If it is determined that the time rate of change of the oxygen sensor temperature is less than the minimum expected time rate of change of the oxygen sensor temperature expected for the power level being applied to the heater (YES), it is determined at 412 that water is in contact with the sensor. If it is determined that the time rate of change of the oxygen sensor temperature is not less than the minimum expected time rate of change of the oxygen sensor temperature expected for the power level being applied to the heater (e.g., dT/dt is greater than or equal to the minimum expected dT/dt) (NO), it is determined at 414 that water is not in contact with the sensor. Following 414, method 400 proceeds to 422, where the oxygen sensor is controlled nominally, as described in further detail below with reference to FIG. 6.

It will be appreciated that other determinations may be performed alternatively or in addition to assessing dT/dt to determine whether water is in contact with the oxygen sensor. For example, if it is determined that dT/dt=0, it may be determined that water is in contact with the oxygen sensor. Further, water contact with the oxygen sensor may be determined if the sensor temperature decreases by at least a threshold amount in a suitable duration. Such temperature decreases may be particularly assessed after nominal oxygen sensor control has been employed at least once. Rapid (e.g., immediate) decreases in oxygen sensor temperature from its operational temperature may indicate water impingement on the sensor (e.g., due to a water splash event). It will also be appreciated that two or more temperature measurements of the oxygen sensor may be determined prior to determining dT/dt so that dT/dt may be sufficiently determined. As dT/dt may be evaluated responsive to the application of the initial power level to the heater, temperature measurement may be performed following 406 but before 410.

Following 412, method 400 proceeds to 416 where the oxygen sensor is controlled based on the determination made at 410 that water is in contact with the sensor. Turning now to FIG. 5, a flowchart illustrating a method 500 of controlling an oxygen sensor based on water contact with the sensor is shown. Method 500 may be employed to control one or more of oxygen sensors 128, 129, and 200 in the event it is determined that water has impinged thereon, for example.

At 502 of method 500, a lower power level is applied to a heater (e.g., heater 207 of FIG. 2) of the oxygen sensor. In some examples, the lower power level is the initial power level applied to the heater at 406 of method 400, in which case the initial power level continues to be applied to the heater after it is determined that water has come into contact with the oxygen sensor. In other examples, the lower power level is greater than the initial power level—for example, the initial power level is a first power level, and the lower power level is a second power level greater than the first power level. Regardless, the lower power level is sufficiently low such that the oxygen sensor does not undergo thermal shock and cracking At 504 of method 500, it is determined whether the expected oxygen sensor temperature has been reached or whether the time rate of change of the oxygen sensor temperature (dT/dt) is greater than or equal to the minimum expected time rate of change of the oxygen sensor temperature ($dT_{ex}$). Both the expected oxygen sensor temperature and the minimum expected time rate of change of the oxygen sensor temperature may be expected for the power being applied to the heater (e.g., the lower/second power level) and one or more environmental conditions. Since the oxygen sensor temperature (and/or time rate of change thereof) may be evaluated responsive to the application of the lower power level to the heater, temperature measurement may be performed following 502 but before 504. Moreover, a determination of the one or more environmental conditions may be made as part of 504; for example, the one or more environmental conditions may include intake airflow, exhaust temperature, etc. A suitable data structure (e.g., lookup table) storing expected oxygen sensor temperatures and/or minimum expected time rates of sensor temperature change for applied heater power levels and the one or more environmental conditions may be accessed as part of 504, for example. If it is determined that the expected oxygen sensor temperature has not been reached or dT/dt is not greater than or equal to the minimum expected dT/dt (NO), method 500 returns to 504. If it is determined that the expected oxygen sensor temperature has been reached or dT/dt is greater than or equal to the minimum expected dT/dt (YES), method 500 proceeds to 506.

At 506 of method 500, the power applied to the heater is increased up to a threshold power level such that the oxygen sensor temperature increases at a maximum allowable rate. In some examples, the applied heater power may be increased (e.g., above the lower/second power level) at a relatively gradual rate—e.g., not immediately from a relatively lower power level to a relatively higher power level. The threshold power level may be a relatively limited power level—e.g., less than a maximum power level but greater than the lower power level and/or the initial power level. The maximum allowable rate at which the oxygen sensor temperature may increase may be less than a rate at which thermal shock and cracking may otherwise be imparted to the oxygen sensor. The threshold power level and/or rate at which the oxygen sensor temperature increases may be selected based on the maximum allowable rate; in some examples, a suitable data structure such as a lookup table may be accessed to select the threshold power level and/or rate of temperature increase based on the maximum allowable rate. In some examples, the applied heater power may be increased if a relatively small quantity of water less than a threshold quantity is inferred to be in contact with the oxygen sensor and if dT/dt remains greater than or equal to $dT_{ex}$. Thus, the applied heater power is not increased if the inferred quantity of water in contact with the oxygen sensor is greater than or equal to the threshold quantity and/or if dT/dt does not remain greater than or equal to $dT_{ex}$. In this case, the applied heater power may remain constant or be reduced until one or both conditions are satisfied.

At 508 of method 500, it is determined whether water is still in contact with the oxygen sensor. Water contact may be determined in the manners described above (e.g., by executing 408 of method 400). If it is determined that water is still in contact with the oxygen sensor (YES), method 500 returns to 506. In this way, the heater power may be continually increased up to the threshold power level as long as water contact on the oxygen sensor is detected. If it is determined that water is not still in contact with the oxygen sensor (NO), method 500 ends.

Returning to FIG. 4, method 400 is resumed at 418 upon termination of method 500, where the power applied to the heater is increased up to a threshold power level such that the oxygen sensor temperature increases at a maximum allowable rate, as at 506 of method 500.

At 420 of method 400, it is determined whether the operational temperature of the oxygen sensor has been reached. The operational temperature may be a temperature that, when reached by the oxygen sensor, enables desired sensing by the sensor (e.g., a light-off temperature). If it is determined that the operational temperature of the oxygen sensor has not been reached (NO), method 400 returns to 418. In this way, the applied heater power may be iteratively increased until the operational temperature of the oxygen sensor is reached but not overshot. As such, the applied heater power may be increased and the oxygen sensor temperature determined at various suitable frequencies and various suitable durations to prevent sensor degradation while minimizing the time spent reaching the operational temperature. If it is determined that the operational temperature of the oxygen sensor has been reached (YES), method 400 proceeds to 422.

At 422 of method 400, the oxygen sensor is controlled nominally. The oxygen sensor is also controlled nominally if it was determined at 414 that water was not in contact with the sensor, as described above. Turning now to FIG. 6, a flowchart illustrating a method 600 of nominally controlling an oxygen sensor is shown. Method 600 may be employed to nominally control one or more of oxygen sensors 128, 129, and 200, for example. In some examples, method 600 may be employed to nominally control an oxygen sensor once its operational temperature has been reached following impingement of water thereon, or if water was determined to not be in contact.

At 602 of method 600, the temperature of the oxygen sensor is determined. The oxygen sensor temperature may be determined in the manners described above—e.g., as determined at 402 of method 400.

At 604 of method 600, a temperature setpoint for the oxygen sensor is determined. The temperature setpoint may be a temperature to which the temperature of the oxygen sensor is desired to correspond; for example, the setpoint may be the operational temperature of the sensor. In some examples, the temperature setpoint may be predetermined, such that determining the setpoint includes retrieving the predetermined setpoint (e.g., by accessing a suitable data structure storing the setpoint).

At 606 of method 600, power is applied to a heater (e.g., heater 207 of FIG. 2) of the oxygen sensor based on the difference between the oxygen sensor temperature determined at 602 and the temperature setpoint determined at 604. More specifically, the power applied to the heater may be may be selected so as to minimize the difference between the sensor temperature and the setpoint so that the sensor temperature is brought into as close correspondence with the setpoint as possible. Controlling the heater power in this way may involve use of closed loop control, for example, where the input is an error (e.g., the difference between the oxygen sensor temperature and the temperature setpoint) and the output is the heater power. Closed loop control may utilize one or more of proportional, integral, and derivative control, for example.

At 608 of method 600, it is determined whether water is in contact with the oxygen sensor. Water contact may be determined in the manners described above (e.g., by executing 408 of method 400). Accordingly, in some examples, two or more determinations of the oxygen sensor temperature may be performed prior to 608. If it is determined that water is not in contact with the oxygen sensor (NO), method 600 returns to 602. If it is determined that water is in contact with the oxygen sensor (YES), method 600 proceeds to 610 where the sensor is controlled based on the determination made at 608 that water is in contact with the sensor. The oxygen sensor may be controlled based on water contact according to method 500 of FIG. 5 described above. Method 600 may end upon vehicle key-off, for example.

It will be appreciated that determination of the oxygen sensor temperature and presence of water contact thereon may be performed at various suitable frequencies and durations. Method 600 may be employed to accurately control the temperature of the oxygen sensor according to a desired temperature setpoint while monitoring the sensor for water contact in real time. If water contact on the oxygen sensor is detected, method 600 enables control of the oxygen sensor to be switched from the nominal control scheme to a control scheme suited for the presence of water contact, avoiding sensor degradation and maximizing the speed with which nominal sensor control is returned to.

FIG. 7 shows a graph 700 illustrating operation of an example oxygen sensor. Graph 700 may particularly illustrate operation of one or more of oxygen sensors 128, 129, and 200 according to methods 400, 500, and 600, of FIGS. 4, 5, and 6, respectively. Generally, graph 700 illustrates how an oxygen sensor may be operated according to heterogeneous control schemes depending on whether water impingement on the sensor is detected.

At the start of graph 700 (e.g., starting at time $t_0$), operation of the oxygen sensor and an associated heater (e.g., heater 207 of FIG. 2) is initiated, for example in response to vehicle key-on. From time $t_0$ to time $t_1$, an initial and relatively low power level is applied to the heater to begin raising the temperature of the oxygen sensor. Throughout this duration, water is in contact with the oxygen sensor, as it is determined during this duration that the time rate of change of the oxygen sensor temperature is less than the time rate of change of the oxygen sensor temperature that is expected for the applied heater power and one or more instant environmental conditions, which is represented in FIG. 7 by dashed lines.

Having determined the presence of water contact on the oxygen sensor by time $t_1$, the oxygen sensor is controlled according to water contact, which includes applying a lower power level to the heater at time $t_2$ that in this example is relatively greater than the initial power level but relatively reduced (e.g., less than a maximum heater power level). As shown, the applied heater power is gradually ramped up from the initial power level to the lower power level from time $t_1$ to time $t_2$ to avoid excessively rapid increases in heater power that might otherwise degrade the oxygen sensor. The lower power level is maintained from time $t_2$ to a time $t_3$, at which point the expected oxygen sensor temperature and/or the minimum expected time rate of change of oxygen sensor temperature, both expected for the applied heater power and the one or more environmental conditions, are reached. From time $t_3$ to a time $t_4$, the applied heater power is increased up to a threshold power level such that the oxygen sensor temperature increases at (or in some examples below) a maximum allowable rate as long as water contact with the sensor is detected. As such, between times $t_3$ and $t_4$, water contact on the sensor may be persistently determined at a suitable frequency. The applied heater power may be increased between times $t_3$ and $t_4$ as long as a relatively low quantity of water is inferred to be in contact with the oxygen sensor and the time rate of change of the sensor temperature is greater than or equal to an expected time rate of change of the sensor temperature. At time $t_4$, water contact on the oxygen sensor is no longer detected, and the applied heater power is increased up to the threshold power level such that the oxygen sensor temperature increases at (or in some examples below) the maximum allowable rate as described above. At time $t_5$, the operational temperature of the oxygen sensor is reached (represented in FIG. 7 by dot-dash lines), and nominal (e.g., closed loop) control of the sensor is engaged. As such, from time $t_5$ and onward, the operational temperature is maintained by the oxygen sensor by adjusting the heater power according to the difference between the actual sensor temperature and a desired temperature setpoint (e.g., the operational temperature).

It will be appreciated that graph 700 is provided as an example and is not intended to be limiting in any way. For example, the form, duration, and timing exhibited by the parameters in FIG. 7 are provided as examples and may be exaggerated for the purpose of illustration.

Implementations may provide a method of controlling an oxygen sensor that includes using the resistance of a heater of the sensor to determine the temperature of the oxygen sensor. Using the heater resistance may facilitate determination of the oxygen sensor temperature at all times during its operation. As such, at substantially no point during sensor operation may the sensor temperature be unknown. This allows the water detection and closed loop control approaches described herein to be implemented on an oxygen sensor. As a result, the time taken for the oxygen sensor to reach its operational temperature may be reduced, decreasing engine emissions.

Implementations may further provide a method of operating an oxygen sensor that comprises applying an initial power level to a heater of the oxygen sensor. The method may further comprise controlling the heater according to a first control scheme responsive to water being in contact with the oxygen sensor. Water contact with the oxygen sensor may be determined from a sensor temperature time rate of change in the manners described above. Otherwise (e.g., if water is determined to not be in contact with the sensor), the heater is controlled according to a second control scheme different from the first control scheme. The first control scheme may include applying a second power level to the heater, where the second power level is greater than the initial power level. The first control scheme may further include indicating whether one of an expected temperature and a minimum expected sensor temperature time rate of change is reached by the oxygen sensor, the expected temperature and the minimum expected time rate of change both expected for the second power level. The first control scheme may further include, responsive to indicating that one of the expected temperature and the minimum expected time rate of change has been reached by the oxygen sensor, increasing the power applied to the heater above the second power level up to a threshold power level so that the temperature of the oxygen sensor increases at a maximum allowable rate. The first control scheme may further include indicating whether water remains in contact with the oxygen sensor, and, responsive to indicating that water remains in contact with the oxygen sensor, increasing the power applied to the heater until indicating that water is no longer in contact with the oxygen sensor. Then, responsive to indicating that water is not in contact with the oxygen sensor, the power applied to the heater may be increased until the temperature of the oxygen sensor reaches an operational temperature. The first control scheme may further include, responsive to the temperature of the oxygen sensor reaching the operational temperature, controlling the heater via closed loop control. Closed loop control may include determining the temperature of the oxygen sensor, determining a temperature setpoint, and applying power to the heater based on a difference between the temperature of the oxygen sensor and the temperature setpoint. Generally, the first control scheme limits the magnitude and rate of increase of power applied to the sensor heater in the presence of water so that excessive increases in heater power that can cause sensor degradation are avoided.

The second control scheme may include determining the temperature of the oxygen sensor, determining a temperature setpoint, and applying power to the heater based on a difference between the temperature of the oxygen sensor and the temperature setpoint. As such, in some examples, the second control scheme may include closed loop control. Generally, the second control scheme may allow the application of greater power levels to the sensor heater relative to the first control scheme, and may be employed to maintain the sensor temperature as close to the temperature setpoint as possible. In some examples, the applied heater power may oscillate as maintenance of the temperature setpoint is sought.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method of operating an oxygen sensor, comprising:
applying power to a heater of the oxygen sensor;
indicating whether water is in contact with the oxygen sensor based on a time rate of change of a temperature of the oxygen sensor;
wherein the power is an initial, first power level, the method further comprising:
responsive to indicating that water is in contact with the oxygen sensor, applying a second power level greater than the first power level to the heater: and
determining whether one of an expected temperature and a minimum expected time rate of change of the temperature of the oxygen sensor is reached by the oxygen sensor, the expected temperature and the minimum expected time rate of change both expected for the second power level.

2. The method of claim 1, wherein indicating whether water is in contact with the oxygen sensor includes indicating that water is in contact with the oxygen sensor responsive to the time rate of change being less than a minimum expected time rate of change of the temperature of the oxygen sensor expected for the power applied to the heater, wherein the minimum expected time rate of change is retrieved by accessing a lookup table with the power being applied to heater.

3. The method of claim 1, further comprising, prior to indicating whether water is in contact with the oxygen sensor, determining the temperature of the oxygen sensor based on:
only a resistance of the heater if the resistance indicates a temperature below or equal to a threshold temperature; and
both the resistance of the heater and an impedance of the oxygen sensor if the resistance indicates a temperature above the threshold temperature.

4. The method of claim 1, wherein the power is at a minimum power level, the minimum power level is a power level that drives heating of the oxygen sensor without causing thermal shock to the oxygen sensor and cracking that otherwise might occur in the presence of water contacting the oxygen sensor while applying power greater than the initial power level.

5. The method of claim 1, wherein the expected temperature and the minimum expected time rate of change are further expected for one or both of intake airflow and exhaust temperature.

6. The method of claim 1, further comprising, responsive to one of the expected temperature and the minimum expected time rate of change being reached by the oxygen sensor, increasing the power applied to the heater above the second power level up to a threshold power level so that the temperature of the oxygen sensor increases at a maximum allowable rate.

7. The method of claim 6, further comprising:
indicating whether water remains in contact with the oxygen sensor;
responsive to indicating that water remains in contact with the oxygen sensor, increasing the power applied to the heater until indicating that water is no longer in contact with the oxygen sensor; and
responsive to indicating that water is not in contact with the oxygen sensor, increasing the power applied to the heater until the temperature of the oxygen sensor reaches an operational temperature.

8. The method of claim 7, further comprising responsive to the temperature of the oxygen sensor reaching the operational temperature, controlling the heater via closed loop control.

9. The method of claim 8, wherein closed loop control includes:
determining the temperature of the oxygen sensor;
determining a temperature setpoint; and
applying power to the heater based on a difference between the temperature of the oxygen sensor and the temperature setpoint.

10. A method of operating an oxygen sensor, comprising:
applying an initial power level to a heater of the oxygen sensor;
indicating whether water is in contact with the oxygen sensor based on a time rate of change of a temperature of the oxygen sensor;
responsive to indicating that water is in contact with the oxygen sensor, controlling the heater according to a first control scheme; and
responsive to indicating that water is not in contact with the oxygen sensor, controlling the heater according to a second control scheme different from the first control scheme.

11. The method of claim 10, wherein the first control scheme includes:
applying a second power level to the heater, the second power level being greater than the initial power level; and
indicating whether one of an expected temperature and a minimum expected time rate of change of the temperature of the oxygen sensor is reached by the oxygen sensor, the expected temperature and the minimum expected time rate of change both expected for the second power level.

12. The method of claim 11, further comprising responsive to indicating that one of the expected temperature and the minimum expected time rate of change has been reached by the oxygen sensor, increasing the power applied to the heater above the second power level up to a threshold power level so that the temperature of the oxygen sensor increases at a maximum allowable rate.

13. The method of claim 12, further comprising:
indicating whether water remains in contact with the oxygen sensor;
responsive to indicating that water remains in contact with the oxygen sensor, increasing the power applied to the heater until indicating that water is no longer in contact with the oxygen sensor; and
responsive to indicating that water is not in contact with the oxygen sensor, increasing the power applied to the heater until the temperature of the oxygen sensor reaches an operational temperature.

14. The method of claim 13, further comprising responsive to the temperature of the oxygen sensor reaching the operational temperature, controlling the heater via closed loop control.

15. The method of claim 14, wherein closed loop control and the second control scheme include:
determining the temperature of the oxygen sensor;
determining a temperature setpoint; and
applying power to the heater based on a difference between the temperature of the oxygen sensor and the temperature setpoint.

16. A method of operating an oxygen sensor, comprising:
applying an initial power level to a sensor heater;
responsive to water being in contact with the oxygen sensor determined from a sensor temperature time rate of change, controlling the sensor heater according to a first control scheme; and
controlling the sensor heater according to a second control scheme different from the first control scheme.

17. The method of claim 16, wherein the first control scheme includes increasing power applied to the sensor heater above the initial power level responsive to one of an expected temperature and a minimum expected time rate of change of the temperature of the oxygen sensor, and
wherein the second, different control scheme includes applying power to the sensor heater based on a difference between a sensor temperature and a temperature setpoint.

18. The method of claim 17, wherein the first control scheme further includes, responsive to one of the expected temperature and the minimum expected time rate of change being reached by the oxygen sensor, increasing power applied to the sensor heater up to a threshold power level so that the sensor temperature increases at a maximum allowable rate, and
wherein the second, different control scheme further includes indicating whether water is in contact with the oxygen sensor.

19. The method of claim 18, wherein the first control scheme further includes, responsive to water not being in contact with the oxygen sensor, increasing power applied to the sensor heater until the sensor temperature reaches an operational temperature.

* * * * *